United States Patent
Saraf et al.

(12) 
(10) Patent No.: US 6,218,175 B1
(45) Date of Patent: Apr. 17, 2001

(54) NANO-DEVICES USING BLOCK-COPOLYMERS

(75) Inventors: Ravi F. Saraf, Briar Cliff Manor; Hemantha K. Wickramasinghe, Chappaqua, both of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/182,874

(22) Filed: Oct. 30, 1998

(51) Int. Cl.[7] .............................. C12M 1/00; C12Q 1/68; C12P 19/34; C07H 19/00; C07H 22/00
(52) U.S. Cl. ..................... 435/283.1; 435/6; 435/91.1; 435/285.2; 435/287.2; 536/22.1; 536/23.1; 536/24.3
(58) Field of Search ................ 435/6, 91.1, 283.1, 435/285.2, 287.2; 536/22.1, 23.1, 24.3

(56) References Cited

U.S. PATENT DOCUMENTS

| | | |
|---|---|---|
| 5,538,898 | 7/1996 | Wickramasinghe et al. . |
| 5,607,568 | 3/1997 | Zenharusern et al. . |
| 5,724,253 | 3/1998 | Skovira . |

*Primary Examiner*—Kenneth R. Horlick
*Assistant Examiner*—Jeffrey Siew
(74) *Attorney, Agent, or Firm*—Pollock, Vande Sande & Amernick; Robert M. Trepp

(57) ABSTRACT

A structure including a substrate. A first electrode and a second electrode are arranged spaced apart from each other on the substrate. A polymer string is positioned on the substrate between the two electrodes, the polymer line has a width of less than about 50 nm.

45 Claims, 2 Drawing Sheets

NANO-DEVICES USING BLOCK-COPOLYMERS

FIELD OF THE INVENTION

The present invention relates to the field of semiconductor chips. In particular, the present invention relates to semiconductor chips that include active device having extremely small feature sizes. The present invention also relates to methods for forming semiconductor chips including active features having such sizes.

BACKGROUND OF THE INVENTION

The shrinking dimensions of active devices on silicon chip is approaching its limit due to restrictions set by photolithographic techniques. For example, wave properties of radiation, such as interference and diffraction, can limit device size and density. Considerable research has taken place to overcome the limitations of photolithographic techniques.

The research has been directed at correcting the problems, such as by phase shift lithography as well as to developing other novel approaches. Concomitantly, with this research, there have been developments in device design utilizing electron confinement in small volume. The three basic categories are such devices design are Quantum Dots (QD), Resonant Tunneling Devices (RTD), and Single Electron Transistors (SET). Quantum Dots are discussed in greater detail in R. Turton, The Quantum Dot, Oxford, U.K., Oxford University Press, 1995; Resonant Tunneling Devices are discussed in greater detail in A. C. Seabaugh et al., Future Electron Devices (FED) J., Vol. 3, Suppl. 1, pp. 9–20, (1993); and Single Electron Transistors are discussed in greater detail in M. A. Kastner, Rev. Mod. Phys., Vol. 64, pp. 849–858, (1992); the entire disclosures of all of which is hereby incorporated by reference.

SUMMARY OF THE INVENTION

Aspects of the present invention provide a structure that includes a substrate. A first electrode and a second electrode are arranged on the substrate. A polymer line is positioned on the substrate between the two electrodes. The polymer line has a width of less than about 50 nm.

Other aspects of the present invention provide a method for forming a structure on a substrate. The method includes providing a first electrode and a second electrode on the substrate. A polymer is deposited between the two electrodes. A voltage is applied between the first electrode and the second electrode.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

BRIEF DESCRIPTION OF THE DRAWINGS

The above-mentioned objects and advantages of the present invention will be more clearly understood when considered in conjunction with the accompanying drawings, in which.

DETAILED DESCRIPTION OF THE INVENTION

The present invention provides methods for overcoming and actually circumventing problems associated with photolithographic techniques as well as the electron confinement devices. The resulting devices are much smaller than those created by the commonly known techniques. Accordingly, the present invention includes a novel fabrication method to make devices on a nanometer scale, or nanodevices.

To create such devices, the present invention utilize the self-organization nature of certain synthetic polymers known as block copolymers. Block copolymers employed according to the present invention typically include at least two monomers. Along these lines, one of the monomers typically includes double bonds after the monomer polymerizes.

However, more than two monomers could be utilized. In fact, any number of monomers could be used according to the present invention. Each monomer typically would form a block length that is similar or the same in each polymer. In spite of this, two or three monomers usually will be used according to the present invention, while four may also be used.

Examples of monomers that may be utilized according to the present invention include monomers that form double bond containing polymers. Examples of such monomers include polyisoprene and polybutadiene. Other monomers include styrene and methylmethacrylate.

An embodiment that utilizes two monomers, monomer A and monomer B, can include a block of $N_A$ units of monomer A and $N_B$ units of monomer B. Monomer A may form a polymer with at least one double bond per monomer. The relative amounts of monomer A and monomer B may vary, depending upon the embodiment. According to one embodiment, with no loss in generality, $N_A < N_B$. The ratio $N_A:N$ may be such that the discreet A phase forms cylindrical miscelles. Typically, $N_A/(N_A+N_B)$ ranges from about 0.15 to about 0.30.

The absolute amount of the monomers may vary, depending upon the embodiment. For example, $N_A$ may be greater than about 1000.

According to an embodiment that includes differential amounts of two monomers may vary, depending upon the desired characteristics of the polymer while carrying out the method of the invention and of the polymer in the finished product. For example, the relative amounts of the monomers and their characteristics, such as for example, molecular weight, among others, may be varied to control the characteristics of the polymer.

Figure 4:
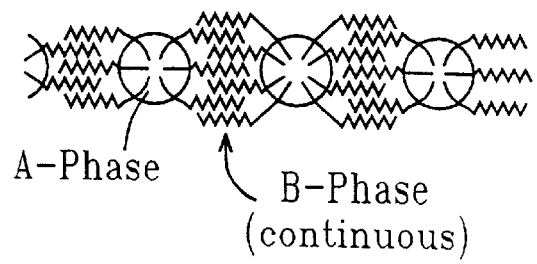
FIG. 4 represents a perspective view of a polymer arrangement in an embodiment of a device according to the present invention.

According to one example, the molecular weight polydispersity, the ratio of weight average molecular weight divided by the number average molecular weight, $P=M_W/M_N$, is low enough such that the system will micro-phase separate to form cylindrical miscelles of monomer A in a continuous phase of monomer B. In such a case, $M_W/M_N$ typically is less than about 1.5. If the polymer arranges itself to form cylindrical miscelles, the cylindrical miscelles may be aligned. FIG. 4 illustrates an example of cylindrical micelles that two polymers, A and B, have formed.

In fact, the relative amounts of the two monomers may be mathematically defines. According to one example, the relationship between the amounts of the two monomers may be characterized by the following relationship, $\phi$:

$$\phi=N_A/(N_A+N_B).$$

In this relationship, $N_A$ and $N_B$ are as defined above. The value of the relationship may vary, depending upon the application. According to one embodiment, $\phi$ has a value in the range of from about 0.15 to about 0.3.

A structure according to the present invention also includes a substrate upon which the nanodevices of the invention may be created upon. The substrate may include a glass. Also, the substrate, whether a glass other form, may include any common semiconductor material. For example, the substrate may include silicon.

Electrodes may be arranged on the substrate. If it is desired to create a polymer line on the substrate, two electrodes may be arranged on the substrate. The electrodes may be formed on the substrate according to common photolithographic techniques.

Additionally, the electrodes B and C may be made of any electrically conducting material. For example, the electrodes may be made of any metal, or alloy. Preferably, the electrodes are made of an oxide-free metal. According to one example, the electrodes are made of gold.

Figure 1A:
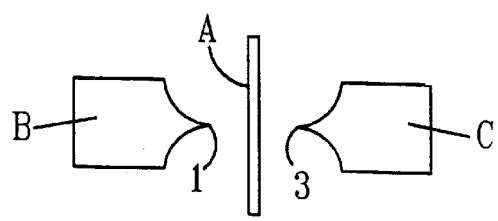
FIGS. 1a–1c represent overhead views and FIG. 1(d) represents a cross-sectional view of an embodiment of a device according to the present invention as it exists at various stages of an embodiment of a process according to the present invention.
Figure 2A:
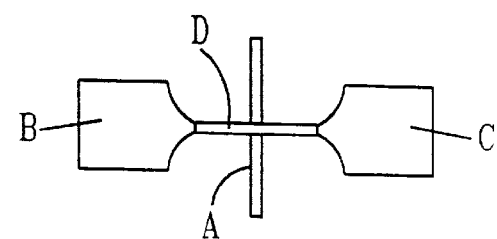
FIG. 2a represents an overhead view and FIGS. 2(b)–2(d) represent cross-sectional views of an embodiment of a device according to the present invention as it exists at various stages during further processing according to an embodiment of a process of the present invention.

FIG. 1(a) illustrates an overhead view of an embodiment of a substrate with two electrodes, B and C, on the surface. The electrodes B and C are in close proximity to each other. The distance between the electrodes may vary, depending upon the embodiment. According to one example, the electrodes may be separated by a distance of from about 1 μm to about 100 μm.

The thickness of the film typically is substantially equal to the diameter of the cylindrical micelles. The diameter of the micelles is typically about 10 nm to about 50 nm for cylindrical micelles such as those illustrated in FIG. 4.

The electrodes may have a variety of shapes, depending upon the embodiment. FIG. 1(a) illustrates an example in which electrodes B and C terminate in points, or apexes, 1 and 3 that face each other. The sides of the points may be curved. For example, the sides of the electrodes could be concave or convex. Alternatively, the sides of the electrodes may be straight. The configuration of the remaining portion of the electrodes may vary, as long as the remaining portion provides an area for connection of a power source to apply power to the electrodes.

The present invention may include a third electrode A. The third electrode may be referred to as a gate electrode. The function of the third electrode will be discussed below in greater detail.

The third electrode may be positioned between the first two electrodes as illustrated in the embodiment shown in FIG. 1(a). The third electrode may also be formed by utilizing common photolithographic techniques, although other techniques may be utilized.

The configuration, such as the shape, of the third electrode may vary, depending upon the embodiment. For example, the third electrode illustrated in FIG. 1(a) is substantially a long, thin rectangle, in other words, substantially a straight line.

The thickness of the third electrode may vary, depending upon the application. For example, the third electrode may have a width of from about 100 nm to about 5000 nm. Preferably, the third electrode is as narrow and thin as possible. According to one embodiment, the third electrode has a thickness of less than about 100 nm.

The dimensions, especially the thickness, of the third electrode may be controlled by a variety of factors. For example, the dimensions of the third electrode may be controlled by the quality of the block copolymer film deposited on the electrodes. Film quality characteristics that may affect dimensions of the third electrode include smoothness and adhesion. According to one embodiment, the third electrode is made as thin as possible to avoid undulations in the film deposited due to the thickness of the third electrode. A thick third electrode could result in the polymer film having a bump in it over the third electrode.

The exact location of the third electrode may vary, depending upon the embodiment. For example, the purpose of the third electrode may control its position. Preferably, the third electrode A is positioned equidistant from the tips 1 and 3 of the two electrodes B and C. According to one embodiment, the third electrode may be arranged such that it is perpendicular to a line connecting the points of electrodes B and C.

As with electrodes B and C, electrode A may be made of any electrically conducting material. For example, the third electrode may be made of any metal, or alloy. Preferably, the third electrode is made of an oxide-free metal. According to one example, the third electrode is made of gold.

After provision of at least the two electrodes B and C, a block copolymer, as described above, may be deposited on the substrate in an area between the two electrodes B and C. The polymer may be deposited utilizing a variety of techniques. According to one example, the polymer is deposited on the substrate by spin coating. According to another example, the block copolymer is solution cast on the substrate.

The polymer may be applied in solution. The solvent may be any suitable solvent that the polymer is soluble in. For example, the solvent may be an organic solvent. The particular solvent typically depends upon the block copolymer system utilized. For example, if the polymer includes styrene-isoprene or styrene-butadiene, the solvent could include a hydrocarbon solvent, such as xylene, toluene, benzene, among others.

The polymer may be applied to an area between the electrodes B and C. The polymer can even entirely cover the electrodes. The excess polymer can always be removed, if necessary. The polymer may also be applied in a layer of any thickness. For example, the thickness of the applied polymer layer may be such that upon evaporation of the solvent, a monolayer of cylinders of the A monomer may be formed.

The solution may be dried by baking in an oven at a temperature of about 20° C. to about 200° C. At least some vacuum or pressure less than atmospheric may be applied to facilitate evaporation.

Subsequent to drying, the remaining polymer film may be subjected to an annealing process. The annealing process may include exposing the polymer to a temperature above its glass transition. The temperature may be well above the glass transition temperature of the polymer.

During the annealing process, the film may be heating to a temperature of about 100° C. to about 300° C. above the glass transition temperature of the block copolymer. The temperature is also appropriate for the polymer to microphase separate from a single phase system into a two phase film with cylindrical miscelles of the minority component surrounded by a continuous matrix of the majority component.

During the annealing process, the polymer may be subjected to an electric field. The strength of the electric field may vary, depending upon the embodiment. For example, the molecular weight and difference in dielectric constant between the two polymeric components of the block copolymers may play a role in determining the strength of the electric field. For example, larger difference in the dielectric constant or smaller molecular weight may require the application of a smaller electric field.

Figure 1B:
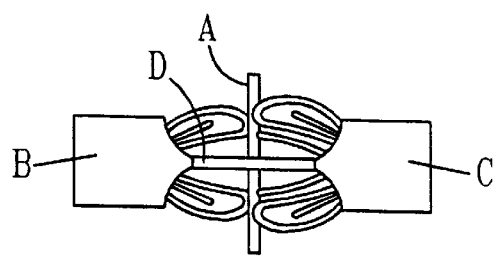

The electric field is sufficiently large to align cylinders of the polymer(s). Alternatively or additionally, the electric field may be small enough that cylinders of the polymer(s) are fully aligned only in a region between the tips of the electrodes B and C. As illustrated in FIG. 1(b), According to one embodiment, the electric field may be above about 20 KV/cm.

The electric field may be created by applying a voltage across the electrodes B and C. The voltage may vary, depending upon the embodiment. Typically, the voltage is sufficiently large to result in the alignment of at least one cylinder of the polymer(s)/monomer(s) between electrodes B and C. FIG. 1(b) illustrates one cylinder D that spans the distance between the points of the two electrodes B and C. At least one cylinder or more may extend between the electrodes. Loops that extend between two points on the same electrode and do not connect electrodes B and C serve no function.

For example, the electric field may be from about 1 kV/cm to about $10^3$ kV/cm.

After the annealing, the polymer may be dry processed to remove matrix material from the surface of the substrate, electrodes or any other surface. This represents all of the polymer and/or monomer material that has not formed cylinders. According to one embodiment, the material may be removed by plasma processing.

The process utilized for removing the matrix material may depend upon the type of polymer(s) being utilized in the process. For example, the matrix material may be removed or etched with a dry process. According to one embodiment, if the polymer utilized in the invention is a double bond containing polymer, such as polyisoprene or polybutadiene, the etching process can be a dry process including ozone exposure.

Figure 1C:
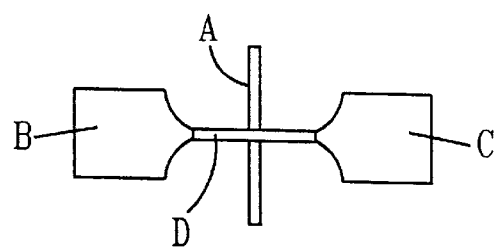
Figure 1D:
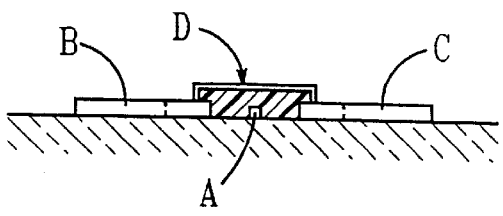

The etching of the matrix material may result in the etching of all of the polymer/monomer except for the portion included in the cylinders. FIG. 1(c) illustrates the appearance of the device after etching. Since only the cylinder(s) between the electrodes spans between electrodes B and C, only that region is shown in FIG. 1(c). However, the other cylinders illustrated in FIG. 1(b) are still there on the substrate. FIG. 1(d) provides a cross-sectional view of the device at the stage shown in FIG. 1(c).

As shown in FIGS. 1(c) and 1(d), the present invention results in the formation of a "polymer wire" between electrodes B and C. In FIGS. 1(c) and 1(d), if any polymer loops remain, they are not shown since they are non-functional. If $N_A$ as defined above is approximately 1000, the width of the wire will be from about 10 nm to about 20 nm. The thickness will be about the diameter of the cylinder. Typically, the electrodes are less than about 1 mm apart. As a result, the absolute voltage is low enough to avoid any dielectric breakdown.

After formation of the polymer wire, processes may be carried out to modify the surface of the wire. For example, at least one metal and/or alloy may be plated on the surface of the polymer wire. The modifications that are performed may depend upon the desired function of the modification (s).

If metal is to be plated on the polymer wire, the plating process may be carried utilizing standard electroless plating processes. For example, plating process may begin with a seeding process. One example of a seeding process seeds palladium on the polymer wire.

According to one embodiment, the seeding process may begin with modifying the surface of the polymer wire with acetate groups or an acid spray. Ion exchange may then be carried out with a palladium salt. Then, a reduction may be carried out on the palladium salt to seed the palladium on the polymer wire utilizing a reducing agent. The seeds/seed layer are represented by E in FIG. 2(b).

Figure 2B:
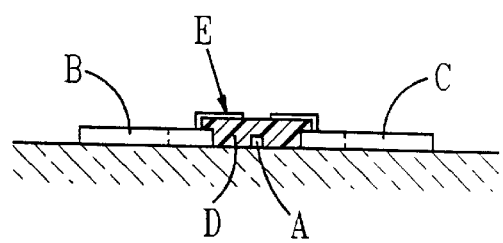

Prior to electroless plating of the complete polymer wire D, metal seeds in a region above electrode A may be removed. Removal of the seeds may be carried out utilizing a variety of processes. For example, the seeds may be removed in this area using an atomic force microscope. The seed may be removed to form a capacitive coupling between the wires on the left and right hand side of the regions where the seeds are removed. FIG. 2(b) illustrates the state of the device at this stage of the process.

Figure 2C:
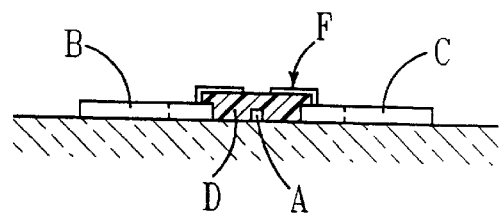

After selective removal of the seeds, metal may be plated on the seeded polymer wire. Any metal and/or allow may be plated on the polymer wire. According to one embodiment, gold is plated on the polymer wire. The plated wire is represented by F in FIG. 2(c).

Figure 2D:
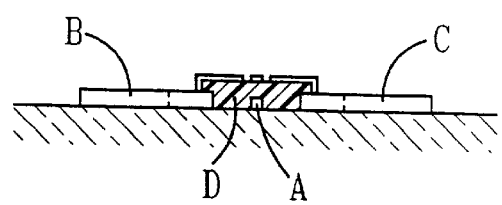

As a result of the removal of the plating seeds in the region over electrode A, the electrolessly plated polymer wire has a break. This broken region can be modified and seeded by similar processes described above and illustrated in FIGS. 2(a)–2(d) to achieve a metal island that is capacitively connected to the polymers wires connected to electrodes B and C. FIG. 2(d) illustrates a seed of palladium in the unplated area.

As a result of the two plated polymer wires separated by the region above electrode A, the current from electrode B to electrode C can thus be regulated by injecting charge in the seed via gate electrode D, the polymer wire.

By imbedding two gate lines, an AND gate may be achieved. Furthermore, similar to previous disclosure two pairs of electrodes can be linked to make an OR gate.

Rather than plate metal(s) on the polymer wire, devices may be created on the polymer wire utilizing a biological polymer, or biopolymer, such as DNA. Typically, the biopolymer has a molecular axis and the molecular axis. The molecular axis of the biopolymer is may be arranged parallel to the polymer string.

The DNA can be deposited and modified as described in U.S. patent application Ser. No. 09/154,575, to the same inventors and assigned to the same assignee of the present application, the entire contents of the disclosure of which is hereby incorporated by reference.

Figure 3A:
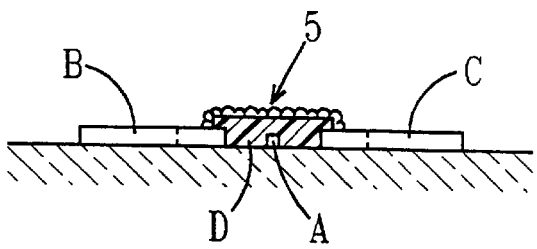
FIG. 3(a) represents a cross-sectional view and FIGS. 3(b) and 3(c) represent overhead views of an embodiment of a device according to the present invention as it exists at various stages during further processing according to an embodiment of a process of the present invention.
Figure 3B:
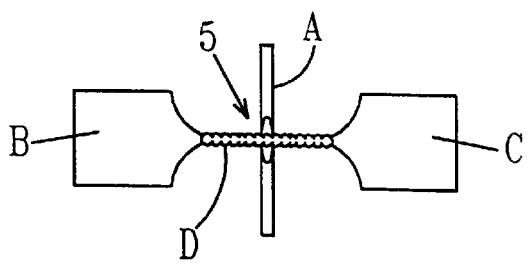
Figure 3C:
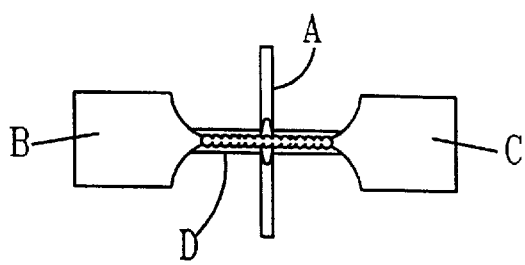

FIGS. 3a–3c illustrate a such a device at various stages of a method for forming the device. According to the method shown in FIG. 3a, at least one DNA molecule may be arranged on a polymer string such as the polymer string described above. At least one R-loop may be formed in the DNA molecule. At least one nanoparticle may be attached to the DNA molecule within the R-loop. The R-loop and the composition of the nanoparticle(s) may be utilized to form a capacitive junction. As such, the nanoparticle(s) may include a metal, a semiconductor, and/or an insulator.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. A structure, comprising:
   a substrate;
   a first electrode and a second electrode spaced apart from each other on the substrate;
   a polymer string positioned on the substrate between the two electrodes, the polymer string having a width of less than about 50 nm; and further comprising a third electrode arranged between the two electrodes perpendicular to the polymer string.

2. The structure according to claim 1, further comprising:
   a seed layer on at least a portion of the polymer string.

3. The structure according to claim 2, wherein the seed layer includes metal particles.

4. The structure according to claim 1, further comprising:
   a biopolymer on at least a portion of the polymer string.

5. The structure according to claim 4, wherein the biopolymer has a molecular axis and the molecular axis of the biopolymer is parallel to the polymer string.

6. The structure according to claim 4, wherein the biopolymer includes DNA.

7. The structure according to claim 1, further comprising:
   nanoparticles bonded to the polymer string.

8. The structure according to claim 7, wherein the nanoparticles include at least one material selected from the group consisting of a metal, a semiconductor, and an insulator.

9. The structure according to claim 1, wherein the third electrode is equidistant from the first electrode and the second electrode.

10. The structure according to claim 1, wherein the third electrode has a width of from about 100 nm to about 5000 nm.

11. The structure according to claim 1, wherein the third electrode has a width of less than 100 nm.

12. The structure according to claim 1, wherein the two electrodes are separated by a distance of from about 1 $\mu$m to about 100 $\mu$m.

13. The structure according to claim 1, wherein the first electrode and the second electrode are made of a material that includes gold.

14. The structure according to claim 1, wherein the first electrode and the second electrode are made of an oxide-free material.

15. The structure according to claim 1, wherein the first electrode and the second electrode terminate in sharp tips that face each other.

16. The structure according to claim 1, wherein the substrate is made of a material that includes a glass.

17. The structure according to claim 1, wherein the polymer string is made of a polymer that includes at least one block copolymer.

18. The structure according to claim 17, wherein the block copolymer includes two monomers.

19. The structure according to claim 18, wherein the block copolymer includes different amounts of the two monomers.

20. The structure according to claim 18, wherein the molecular weight polydispersity of the block copolymer is sufficiently low such that the system will micro-phase separate to form cylindrical miscelles of the two monomers.

21. The structure according to claim 1, wherein the polymer string includes a plurality of aligned cylindrical miscelles of two monomers.

22. The structure according to claim 21, wherein the polymer cylindrical miscelles are fully aligned only in a region between the two electrodes.

23. The structure according to claim 1, wherein the polymer string includes a double bond containing polymer.

24. The structure according to claim 23, wherein the polymer is polyisoprene or polybutadiene.

25. The structure according to claim 19, wherein the amounts of the two monomers is defined by the following equation:

$$\phi = N_A / (N_A + N_B)$$

wherein $\phi$ represents the ratio of the polymers, $N_A$ represents the amount of the first monomer, and and $N_B$ represents the amount of the second polymer.

26. The structure according to claim 25, wherein $\phi$ has a value of between about 0.15 and about 0.3.

27. The structure according to claim 1, wherein the polymer string has a width of from about 10 nm to about 20 nm.

28. The structure according to claim 25, wherein $N_A$ is about 1000.

29. The structure according to claim 24, wherein the third electrode is equidistant from the first electrode and the second electrode.

30. The structure according to claim 24, wherein the third electrode has a width of from about 100 nm to about 5000 nm.

31. The structure according to claim 24, wherein the third electrode has a width of less than 100 nm.

32. A structure comprising:
   a substrate;
   a first electrode and a second electrode spaced apart from each other on the substrate;
   a polymer string positioned on the substrate between the two electrodes, the polymer string having a width of less than about 50 nm; and
   wherein the polymer is polyisoprene or polybutadiene.

33. The structure according to claim 32, further comprising:
   a seed layer on at least a portion of the polymer string.

34. The structure according to claim 33, wherein the seed layer includes metal particles.

35. The structure according to claim 33, further comprising:

a biopolymer on at least a portion of the polymer string.

36. The structure according to claim 35, wherein the biopolymer has a molecular axis and the molecular axis of the biopolymer is parallel to the polymer string.

37. The structure according to claim 35, wherein the biopolymer includes DNA.

38. The structure according to claim 32, further comprising:

nanoparticles bonded to the polymer string.

39. The structure according to claim 38, wherein the nanoparticles include at least one material selected from the group consisting of a metal, a semiconductor, and an insulator.

40. The structure according to claim 32, wherein the two electrodes are separated by a distance of from about 1 m to about 100 m.

41. The structure according to claim 32, wherein the first electrode and the second electrode are made of a material that includes gold.

42. The structure according to claim 32, wherein the first electrode and the second electrode are made of an oxide-free material.

43. The structure according to claim 32, wherein the first electrode and the second electrode terminate in sharp tips that face each other.

44. The structure according to claim 32, wherein the substrate is made of a material that includes a glass.

45. The structure according to claim 32, wherein the polymer string has a width of from about 10 nm to about 20 nm.

* * * * *

UNITED STATES PATENT AND TRADEMARK OFFICE
CERTIFICATE OF CORRECTION

PATENT NO. : 6,218,175 B1
DATED : April 17, 2001
INVENTOR(S) : Ravi F. Saraf et al.

It is certified that error appears in the above-identified patent and that said Letters Patent is hereby corrected as shown below:

<u>Column 3,</u>
Line 16, change "defines" to -- defined --.

<u>Column 6,</u>
Line 64, delete "a" (first occurrence).

<u>Column 9,</u>
Line 15, change "m" to -- nm --.
Line 16, change "m" to -- nm --.

Signed and Sealed this

Sixteenth Day of April, 2002

Attest:

JAMES E. ROGAN
*Director of the United States Patent and Trademark Office*

*Attesting Officer*